(12) United States Patent
Beyer et al.

(10) Patent No.: US 9,907,630 B2
(45) Date of Patent: Mar. 6, 2018

(54) METHOD FOR PRODUCING DENTURES COMPRISING SHORTENING BY MACHINING OF PRE-FABRICATED TOOTH BLANKS

(71) Applicant: Heraeus Kulzer GmbH, Hanau (DE)

(72) Inventors: Mario Beyer, Bad Homburg (DE); Uwe Böhm, Hanau (DE)

(73) Assignee: Kulzer GmbH, Hanau (DE)

( * ) Notice: Subject to any disclaimer, the term of this patent is extended or adjusted under 35 U.S.C. 154(b) by 595 days.

(21) Appl. No.: 14/390,299

(22) PCT Filed: Apr. 18, 2013

(86) PCT No.: PCT/EP2013/058111
§ 371 (c)(1),
(2) Date: Oct. 2, 2014

(87) PCT Pub. No.: WO2013/156572
PCT Pub. Date: Oct. 24, 2013

(65) Prior Publication Data
US 2015/0066181 A1    Mar. 5, 2015

(30) Foreign Application Priority Data
Apr. 19, 2012  (DE) .................. 10 2012 007 706

(51) Int. Cl.
  *A61C 13/00*  (2006.01)
  *A61C 13/36*  (2006.01)
  *B33Y 50/02*  (2015.01)

(52) U.S. Cl.
CPC ...... *A61C 13/0019* (2013.01); *A61C 13/0004* (2013.01); *A61C 13/0022* (2013.01); *A61C 13/1016* (2013.01); *A61C 13/0013* (2013.01); *B33Y 50/02* (2014.12)

(58) Field of Classification Search
None
See application file for complete search history.

(56) References Cited

U.S. PATENT DOCUMENTS

2008/0050700 A1* 2/2008 Weber ............... A61C 13/0004
                                                       433/202.1
2012/0258430 A1    10/2012 Ruppert et al.

FOREIGN PATENT DOCUMENTS

| DE | 3715106 A1 | 11/1988 |
|---|---|---|
| DE | 102009056752 A1 | 6/2011 |
| WO | 2012/021816 A2 | 2/2012 |

OTHER PUBLICATIONS

International Search Report for International Application No. PCT/EP2013/058111 dated Jul. 24, 2013.

* cited by examiner

*Primary Examiner* — Eric C Wai
(74) *Attorney, Agent, or Firm* — Norris McLaughlin & Marcus, P.A.

(57) ABSTRACT

A method produces one or more dentures wherein the dentures have a base element that holds at least two tooth blanks. The method comprises producing a negative mold by machining on the basis of a digital image of a tooth situation and shortening, by machining, a length dimension of the tooth blanks that are preassembled and held in the negative mold from a basal side in order to achieve a tooth line adapted to the tooth situation. The method also comprises connecting the base element and the shortened tooth blanks to form the dentures.

14 Claims, 5 Drawing Sheets

METHOD FOR PRODUCING DENTURES COMPRISING SHORTENING BY MACHINING OF PRE-FABRICATED TOOTH BLANKS

This application is a 371 application of PCT/EP2013/058111 filed 18 Apr. 2013, which claims foreign priority benefit under 35 U.S.C. § 119 of German Application No. DE 10 2012 007 706.8 filed 19 Apr. 2012.

The invention relates to a method for producing a denture.

The state of the art knows so-called partial or total prostheses which can be removed reversibly from the jaw, if applicable. In general, said partial or total prostheses are connected to the jaw and/or an implant introduced into the jaw by means of negative pressure, adhesion or screws. For this purpose, said prostheses comprise a base that comes to rest on the gingiva. Individual teeth are applied to said base—also called base element—as replacement for the natural teeth. Specifically the positioning and introduction of the artificial teeth in and into the base element has proven to be problematic according to the prior art. The artificial teeth used in this context are pre-assembled teeth. Accordingly, the teeth need to be shortened to the lengths actually used. To ensure adaptation to the individually required tooth lengths and widths, it is feasible, firstly, to produce a very large number of different artificial teeth to reflect the most commonly used lengths and/or widths. However, this is very expensive and laborious. Alternatively, it is possible to individually grind down the individual tooth blanks of those artificial teeth, which are inserted into the base element later on. However, it has been evident with this type of method that the accuracy of fit thus attained is too low. Moreover, there is the danger of the tooth blanks, which are multi-layered in structure, to get damaged to the extent that the durability of the denture thus produced is clearly reduced.

It is the object of the present invention to overcome the afore-mentioned disadvantages. In particular, a method is to be disclosed that can be used to produce dentures for a large number of people without involving the risk of the dentures getting damaged during individual adaptation of the tooth blanks to an extent that would lastingly compromise the durability of the denture. To solve said objective, the invention proposes a method for producing a denture having the features of independent claim 1. Moreover, a negative mould and a denture are proposed to solve said objective. Advantageous refinements of the invention, which can be implemented alone or in combination, are presented in the dependent claims. Features and details that are described in the context of the method or the negative mould or the denture shall also apply accordingly to the other embodiments and/or implementations of the invention.

In summary, the following embodiments are proposed as being particularly preferred in the scope of the present invention:

EMBODIMENT 1

Method for producing a denture, whereby the denture comprises a base element, which holds at least two tooth blanks, comprising the steps:
  producing, by machining, a negative mould based on a digital image of a tooth situation;
  shortening, by machining, a length dimension of the tooth blanks that are being held in the negative mould and are pre-fabricated, from a basal side in order to attain a tooth line that is adapted to the tooth situation;
  connecting the base element and the shortened tooth blanks to form the denture.

EMBODIMENT 2

Method according to the preceding embodiment, characterised in that, for preparing the negative mould, a computer-based up-building production method is used, in particular in that the computer-based up-building production method is selected from the group consisting of: rapid prototyping, SD lithography, SLM (selective laser melting), 3D stereolithography, 3D inkjet, FDM (fused deposition modelling), and 3D laser lithography or at least two thereof.

EMBODIMENT 3

Method according to at least one of the preceding embodiments, characterised in that the pre-fabricated tooth blanks are held in the negative mould in a nonpositive fit and/or form closure and/or material bonded manner.

EMBODIMENT 4

Method according to at least one of the preceding embodiments, characterised in that the method comprises the step of:
  preparing an attachment means for connecting the shortened tooth blanks to the base element, whereby the attachment means comprises a first coding means that facilitates definite spatial positioning of the shortened tooth blank in said base part.

EMBODIMENT 5

Method according to at least one of the preceding embodiments, characterised in that the negative mould is provided with at least one second coding means that facilitates definite spatial positioning of the pre-fabricated tooth blank in the negative mould.

EMBODIMENT 6

Method according to at least one of the preceding claims, characterised in that the method comprises the following steps of:
a) preparing the digital image of a tooth situation;
b) computer-based generating of a digital model of the denture based on the digital image;
  by means of using and selecting digital representations of pre-fabricated tooth blanks;
  whereby the pre-fabricated tooth blanks have a defined length dimension;
c) calculating a length difference data set, prepared from the defined length dimension and an insertion depth of the at least two pre-fabricated tooth blanks in the base element.

EMBODIMENT 7

Method according to at least one of the preceding claims, characterised in that the method comprises the following steps of:
d) building-up a digital image of the negative mould, in which the at least two pre-fabricated tooth blanks form the positive, whereby the negative mould encodes the position of the at least two pre-fabricated tooth blanks on the base element;

e) producing, by machining, the negative mould by means of the digital image of the negative mould;
f) inserting the pre-fabricated tooth blanks into the negative mould;
g) shortening, by machining, the length dimension of the pre-fabricated tooth blanks from a basal side based on the length difference data set in order to produce the shortened tooth blanks;
h) connecting the base element and the shortened tooth blanks to form the denture.

EMBODIMENT 8

Method according to any one of the preceding embodiments 6 or 7, characterised in that, in step b), the selection from a number of digital representations of pre-fabricated tooth blanks is done in order to minimise the deviation of a geometrical shape of the pre-fabricated tooth blanks from the tooth situation.

EMBODIMENT 9

Method according to any one of the preceding embodiments 6 or 7, characterised in that, in step b), the selection from a number of digital representations of pre-fabricated tooth blanks is done in order to minimise the deviation of a geometrical shape of the pre-fabricated tooth blanks from a pre-defined tooth arrangement.

EMBODIMENT 10

Method according to at least one of the preceding embodiments 6 to 9, characterised in that, in step c), the selected digital representations of pre-fabricated tooth blanks are arranged as a dental arch.

EMBODIMENT 11

Method according to at least one of the preceding embodiments 6 to 10, characterised in that, in step c), the selected digital representations of the tooth blanks are arranged on a crown side along a tooth line based on the tooth situation and/or a pre-defined tooth arrangement.

EMBODIMENT 12

Method according to at least one of the preceding embodiments 6 to 12, characterised in that the method comprises, after step b), the step of: adapting a height position of the digital representations of the pre-fabricated tooth blanks in the digital model of the denture.

EMBODIMENT 13

Method according to at least one of the preceding embodiments 6 to 12, characterised in that the method comprises the step of: computer-based splitting of the digital model of the denture into a digital image of the base element and a digital likeness of the at least two tooth blanks.

EMBODIMENT 14

Method according to preceding embodiment 13, characterised in that the digital image forms a negative for the negative mould.

EMBODIMENT 15

Method according to preceding embodiment 13, characterised in that the method comprises the step of: fabricating, by machining, the base element based on the digital image of the base element.

EMBODIMENT 16

Method according to at least one of the preceding embodiments, characterised in that the negative mould is provided with at least one positioning element to allow the negative mould to be positioned during the shortening of the length dimension by machining.

EMBODIMENT 17

Method according to at least one of the preceding embodiments, characterised in that the base part comprises a material or consists of a material selected from the group: polyethylene, polypropylene, polystyrene, poly(methylmethacrylate), acrylonitrile-butadiene-styrene copolymer, epoxy or acrylates.

EMBODIMENT 18

Method according to at least one of the preceding embodiments, characterised in that the base part and the shortened tooth blanks are connected in a nonpositive fit and/or form closure and/or material bonded manner.

EMBODIMENT 19

Method according to at least one of the preceding embodiments, characterised in that an attachment means serves to connect the base element and the shortened tooth blanks, whereby the attachment means is selected from the group consisting of: an adhesive, a mechanical connecting means, a screw, a thread, a pin, a bayonet closure or at least two thereof.

EMBODIMENT 20

Method according to at least one of the preceding embodiments, characterised in that an ablating and/or up-building computer-based production method selected from the group consisting of: preparing the negative mould by machining, shortening the length dimension, and fabricating the base element by machining, is used in at least one of the procedural steps of the method.

EMBODIMENT 21

Method according to the preceding embodiment 20, characterised in that the up-building computer-based production method is selected from the group consisting of: rapid prototyping, 3D laser lithography, 3D lithography, SLM (selective laser melting), 3D stereolithography, 3D inkjet, FDM (fused deposition modelling), and 3D laser lithography or at least two thereof.

EMBODIMENT 22

Method according to at least one of the preceding embodiments, characterised in that a digital image of a tooth situation that reflects the shape of a gingival area of a patient is used for shaping the digital model of the denture.

EMBODIMENT 23

Method according to at least one of the preceding embodiments, characterised in that the digital model is obtained by scanning an impression model of the gingival area or by scanning the gingival area of a patient.

EMBODIMENT 24

Computer-readable data medium that comprises instructions that trigger a computer to run a method according to anyone of the preceding embodiments.

EMBODIMENT 25

Computer with a computer-readable data medium according to preceding embodiment 24.

The production of a negative mould is the core of the method according to the invention. The teeth in natural arrangement in the jaw of the patient and/or the desired arrangement of the artificial tooth blanks in the mouth are the positive for said negative mould. In so far, the negative mould comprises all information regarding the position and length of the teeth in the jaw of the patient. The invention then provides pre-produced tooth blanks to be inserted into the negative mould and to be adapted to the requisite length by means of an ablating method. The negative mould therefore protects the surface of the artificial tooth blanks and concurrently ensures that these can be adapted to the desired length. The special feature being that rather than individually adapting single teeth, a plurality of artificial teeth can be processed in parallel. Concurrently, the pre-fabricated tooth blanks being held firmly in the negative mould provides for higher precision of the tooth length to be attained as compared to known methods. Moreover, it can be made sure in the scope of the present method that the tooth blanks are not processed to be shorter than any minimal lengths in order not to destroy their multi-layered structure.

In the scope of the invention, the terms, "tooth blank" or "pre-fabricated tooth blank", shall refer to an element that is equivalent to a natural tooth in terms of its shape and external appearance. Tooth blanks of this type are usually made from plastic materials. High-quality tooth blanks undergo a multi-layered build-up. The layers are polymerised individually in the hot polymerisation process in this context: First the dentine core and then the cutting and enamel layer. Each of said elements of the tooth blank can be built-up from a different plastic material. Due to the multi-layered structure, it is feasible to adapt the technical properties in a layer-specific manner. Accordingly, the cutting enamel layer, which is exposed to high mastication loads, needs to be highly abrasion-resistant. In contrast, the basal neck layer should be less densely cross-linked and more easily detachable for optimal bonding to the plastic material of the prosthesis—i.e. the plastic material of the base element.

The term, "basal", shall be understood according to the invention to mean the root side of the tooth blanks. A shortened tooth blank is a basally processed tooth blank and/or pre-fabricated tooth blank.

The method according to the invention serves for producing dentures. The term, "dentures", shall be understood to mean, in particular, partial prosthesis and total prostheses. A partial prosthesis can be made in various versions. The simplest version consists of a plastic base—the base element—and the teeth to be replaced and curved holding and supporting elements. In case of need, the prosthesis can be reinforced by means of an incorporated wire or bar. Chromium-cobalt-molybdenum as alloy or titanium can be used for parts of the base element as these are particularly compatible with the tissues. Plastic material and teeth are then built-up on said base. If all teeth have been lost from a jaw, a total prosthesis is the only remaining solution in many cases. These are attached to the jaw by means of negative pressure, screws and/or adhesion.

The invention proposes to use an up-building computer-based production method to prepare the negative mould. Said up-building computer-based production method is advantageously selected from the group consisting of: rapid prototyping, 3D laser lithography, 3D lithography, SLM (selective laser melting), 3D stereolithography, 3D inkjet, FDM (fused deposition modelling) or 3D laserlithography. The up-building production methods specified above comprise a number of advantages. Using them, it is easy to produce a negative mould based on a digital image of a tooth situation. Such computer programmes can convert the digital image of the tooth situation into a negative mould in a short period of time. Moreover, the production-related deviations from the digital image of the negative mould are minor. Precision levels on the order of magnitude of +/−20 μm, in particular +/−10 μm, can be implemented using the afore-mentioned production methods. This ensures that the pre-fabricated tooth blanks are held in place in the negative mould with an error of +/−20 μm, in particular +/−10 μm, only. This, in turn, has a positive impact on the shortened tooth blanks being held in place in the denture later on and on the comfort of wear experienced by the patient.

Advantageously, the pre-fabricated tooth blanks are held in place in the negative mould in a nonpositive fit and/or form closure and/or material bonded manner. It is an essential aspect in this context that the pre-fabricated tooth blanks can be detached reversible, but are arranged in the negative mould such as to be stably placed in their position. Appropriate material bonded connections by means of adhesives or magnets enabling the tooth blanks to be positioned and held in place appropriately have proven to be advantageous. Moreover, it is advantageous for the negative mould to be provided with at least one second coding means that facilitates definite spatial positioning of the pre-fabricated tooth blank in the negative mould. A second coding means can, for example, be a projection which engages and/or communicates with a corresponding counter-element in the pre-fabricated tooth blank. This ensures a definite arrangement of the pre-fabricated tooth blanks in the negative mould. In particular inadvertent switching of the front and back side of the tooth blanks is thus prevented.

Moreover, it has proven to be advantageous for the base element to be provided with an attachment means. Said attachment means serves to hold the shortened tooth blanks in place in the base part. Moreover, the attachment means is designed such that it comprises a first coding means that facilitates a definite spatially arrangement of the tooth blank in the base part. This is to ensure that the shortened tooth blanks are inserted into the base part in definite manner exclusively and that they can be arranged therein in a nonpositive fit and/or form closure and/or material bonded manner. Advantageously, the attachment means and/or the base part is/are designed appropriately such that the shortened tooth blank can be arranged in said base part at a positional accuracy of +/−20 μm, advantageously of +/−10 μm. In this context, the attachment means can be designed in a variety of ways, such as, for example, as a bayonet closure, a thread or a pin, which ensure the definite spatial arrangement of the shortened tooth blanks.

In the scope of another advantageous variant of an embodiment, a step a) involves the preparation of the digital image of a tooth situation. A corresponding digital image can be prepared, for example, using an intraoral scanner directly on the patient. Alternatively, it is feasible just as well to take an impression of the patient's tooth situation with an impression mass and to then realise a positive. Corresponding positives can be digitally imaged at high precision using industrial scanners. A digital model of the denture is then generated in a computer-based manner based on said digital image of the tooth situation. Building on said digital model, corresponding digital files and/or models are then used to prepare a denture specifically for said patient. In this context, the invention provides for the use and selection of digital representations of pre-fabricated tooth blanks. The underlying rationale is that only a comparatively small number of pre-fabricated tooth blanks is to be utilised. These are scanned digitally and provided, in the form of a database, to the user preparing the digital model. Using a corresponding selection method, the user can utilise the digital representations of the pre-fabricated tooth blanks to produce the digital model of the denture. Criteria such as size, width, and colour contribute to the selection of the pre-fabricated tooth blanks to be used. The length dimensions of the pre-fabricated tooth blanks are usually not compatible with the lengths of the tooth blanks as actually used that are to be incorporated into the actual denture. Accordingly, the scope of step c) includes the calculation of a length difference data set that results from the difference between the defined length dimension of the pre-fabricated tooth blanks and the insertion depth of the at least two pre-fabricated tooth blanks in the base element. The length difference data set therefore describes the difference between the "actual condition" of the pre-fabricated tooth blanks and the "nominal condition" these are to have upon insertion into the base element.

As illustrated, a selection of digital representations of pre-fabricated tooth blanks proceeds in step b). Said selection from a number of digital representations of pre-fabricated tooth blanks can proceed in order to minimise the deviation of a geometrical shape of the pre-fabricated tooth blanks from the tooth situation actually present in the patient's mouth. This is the case, if the teeth still present are extracted from the mouth of the patient and replaced by the tooth blanks to be inserted. If the patient is toothless, the goal must be to select the digital representations of the pre-fabricated tooth blanks appropriately such that the deviation of a geometrical shape of the pre-fabricated tooth blanks from the tooth arrangement pre-defined ahead of time is minimised. Accordingly, one tooth blank each, which optimally fits into the overall scope of the denture to be produced, is selected. In this context, the size, geometrical shape, and distance from/placement with respect to its neighbours will be crucial.

Another advantageous variant of an embodiment of the method according to the invention is characterised in that it comprises a step d), in the scope of which a digital image of the negative mould is being built up. This digital image serves as the basis for producing, by machining, the actual negative mould later on (see step e)). In this context, the invention provides the negative mould to encode the position of the at least two pre-fabricated tooth blanks on the base element, which also is still to be prepared. Accordingly, the negative mould defines the position of the pre-fabricated tooth blanks with respect to each other and with respect to the element or elements of the base element. The negative mould is prepared by machining in the scope of a step e). Said preparation by machining is effected by means of the digital information of the digital image of the negative mould. A corresponding preparation can proceed by means of ablating or up-building computer-based production methods. Especially the following production methods shall be mentioned in this context: milling, milling by CAD/CAM, turning, rapid prototyping, 3D laserlithography, 3D lithography, SLM (selective laser melting), 3D stereolithography, 3D inkjet, FDM (fused deposition modelling) or 3D laserlithography.

According to the invention, the scope of step g) includes shortening, by machining, the length dimensions of the pre-fabricated tooth blanks from a basal side. After preparation of the negative mould, the pre-existing pre-fabricated tooth blanks are inserted into the negative mould in the scope of step f). The negative mould now serves in holding the pre-fabricated tooth blanks. Since the negative mould is being produced based on the desired digital image of the denture to be prepared, the negative mould concurrently encodes for the arrangement, length, and height of the tooth blanks to be used. Once these are inserted, it is easy to shorten them by machining. Said shortening on the basal side is done based on the length difference data set. Accordingly, the pre-fabricated tooth blanks are shortened exactly by the fraction of length by which they project beyond the desired length. Subsequently, the scope of step h) only includes that the base element and the shortened tooth blanks are connected to form the denture.

Another variant of an embodiment of the method according to the invention provides the digital model of the denture to be split into two parts in computer-based manner: a digital image of the base element and a digital likeness of the at least two tooth blanks. The aim being to also design the base element in computer-based manner. In particular, this variant enables very good adaptation of the base element and tooth blanks and/or digital representations of the pre-fabricated tooth blanks. Moreover, digital models of attachment means, etc., can be incorporated into the digital image of the base element. Also, the digital representation of the pre-fabricated tooth blanks is adapted in terms of its position with respect to the base element. Said adaptation of a height position of the digital representation of the pre-fabricated tooth blanks permits the digital model of the denture to be designed on a computer. The adaptation of the height position also involves the calculation of the length difference data set, since the adaptation of the height position provides feedback concerning the depth by which the pre-fabricated tooth blanks are to be inserted into the base element later on.

Based on the digital image of the base element, it is feasible to fabricate the actual base element by machining. Ablating just as well as up-building computer-based production method can be used for this purpose. Accordingly, milling, turning or sawing can be used for an ablating production method. The up-building production methods mentioned above, which are used in the production of the negative mould, can also be used for production of the base element.

Further measures and advantages of the invention are evident from the claims, the description provided hereinafter, and the drawings. The invention is illustrated through several exemplary embodiments in the drawings. In this context, equal or functionally equal or functionally corresponding elements are identified through the same reference numbers. The invention shall not be limited to the exemplary embodiments.

Figure 1:
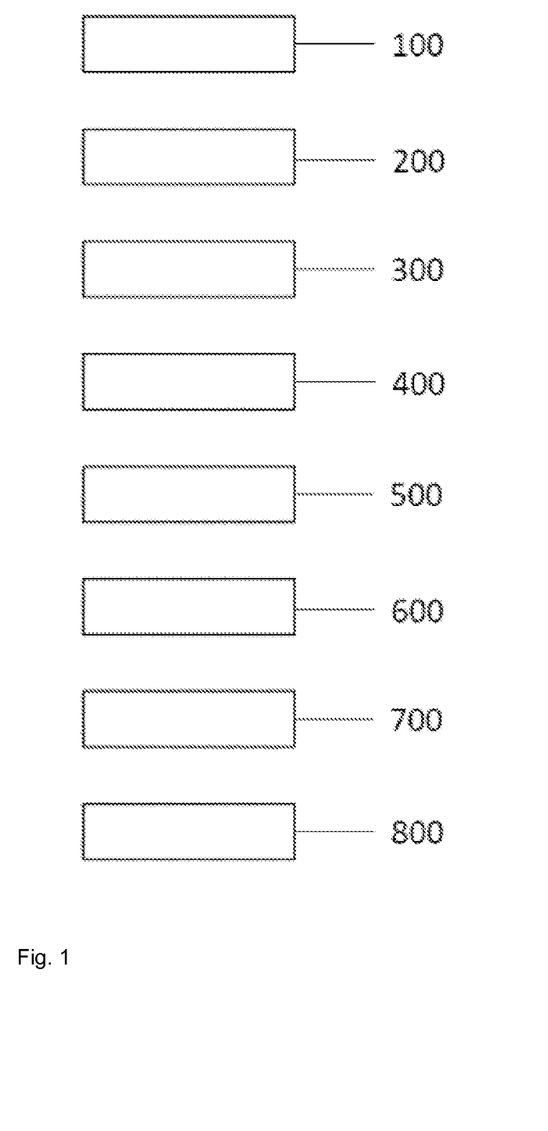
FIG. 1 shows a flow diagram of the method according to the invention.

The underlying rationale of the method according to the invention is to prepare a negative mould 50 that serves to support a plurality of pre-fabricated tooth blanks 40, 40', 40". The negative mould 50 is designed appropriately in this context such that the tooth blanks 40, 40', 40" are positioned in it in the same way in which they are to be arranged in the denture 10 later on. In this context, the lengths of the pre-assembled tooth blanks 40, 40', 40" do not correspond to the lengths as needed in the actual denture 10 that is still to be produced. However, since they are being held in the negative mould 50, the pre-fabricated tooth blanks 40, 40', 40" can be shortened at high precision. Moreover, the method according to the invention has a particularity in that the negative mould 50 is calculated from a digital image of a tooth situation 15 by means of a computer. The flow diagram shown in FIG. 1 is to illustrate the various procedural steps of the method.

Figure 2:
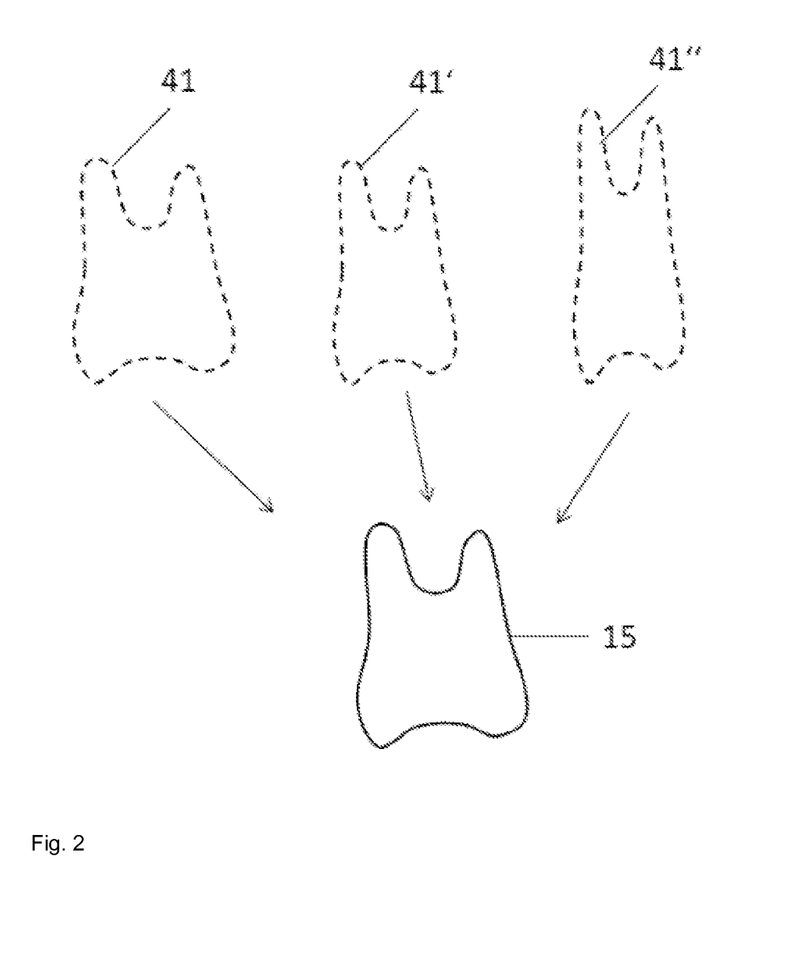
FIG. 2 shows a process of selecting digital representations of pre-fabricated tooth blanks.

In step 100, a digital image of the existing tooth situation 15 of the patient is prepared. This can be done, preferably, by means of an intraoral scanner. Subsequently, a digital model 11 of the denture 10 to be produced is produced based on the digital image. If, for example, a total prosthesis is to be prepared, an image of only the gingiva is generated in the scope of the digital image of the tooth situation. Based on said image of the gingiva, a dental technician then needs to digitally prepare the denture 15 to be inserted later. According to the invention, the dental technician can use digital representations 41, 41', 41" of pre-fabricated tooth blanks 40, 40', 40" for this purpose. The digital model 11 of the denture 10 is prepared in the scope of step 200. FIG. 2 illustrates in exemplary manner that a selection is being made of which of the digital representations 41, 41', 41" of a pre-fabricated tooth blank 40, 40', 40" corresponds best to the desired tooth situation 15. In this context, in particular the size, length, and volume are used as selection criteria.

Figure 3:
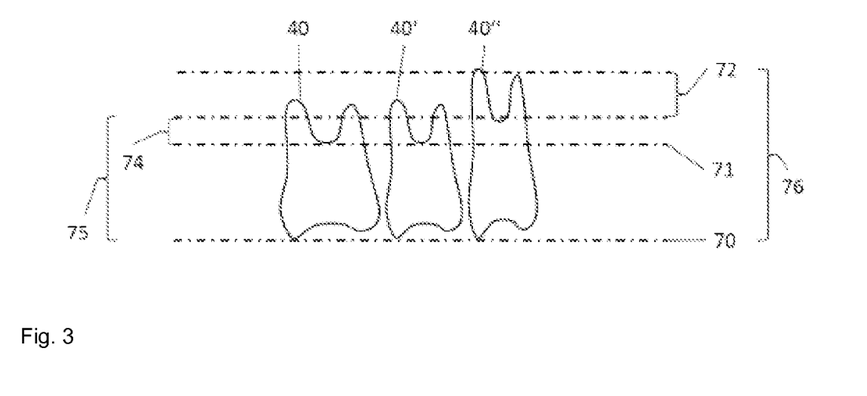
FIG. 3 shows a calculation of a length difference data set.

After calculation of the shape of the digital model 11 and selection of the digital representations 41, 41', 41" of the pre-fabricated tooth blanks 40, 40', 40" in step 200, a length difference data set 72 is determined in step 300. This is to be illustrated in FIG. 3. The length of the teeth is different between humans due to the difference in anatomical situations. The pre-fabricated tooth blanks 40, 40', 40" all have the same pre-defined lengths, though. Moreover, it is known to which depth the tooth blanks need to be inserted into the base element for the assembly to be stable and non-reversible. This depth is called insertion depth 74 and it is pre-defined and it is a function of the dimension of the base element 20. The distance between a base line 70, on which the cutting surface of the teeth is arranged, and a capital line 71 defines the visible length of the pre-fabricated tooth blanks 40, 40', 40". The insertion depth 74 is directly adjacent to this. The desired tooth length 75 results from the two lengths. In FIG. 3, in exemplary manner, the actual tooth length 76 of the pre-fabricated tooth blank 40" differs strongly from said desired tooth length 75. The length difference data set 72 is calculated from the desired tooth length 75 and the actual tooth length 76 in the scope of step 300.

Figure 4:
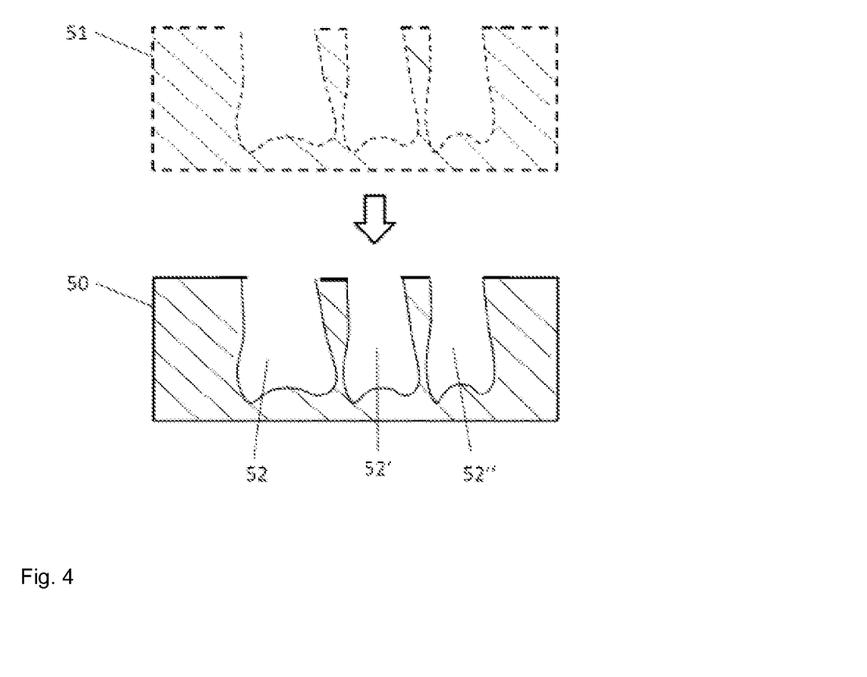
FIG. 4 shows a process of inserting the pre-fabricated tooth blanks into a negative mould.
Figure 5:
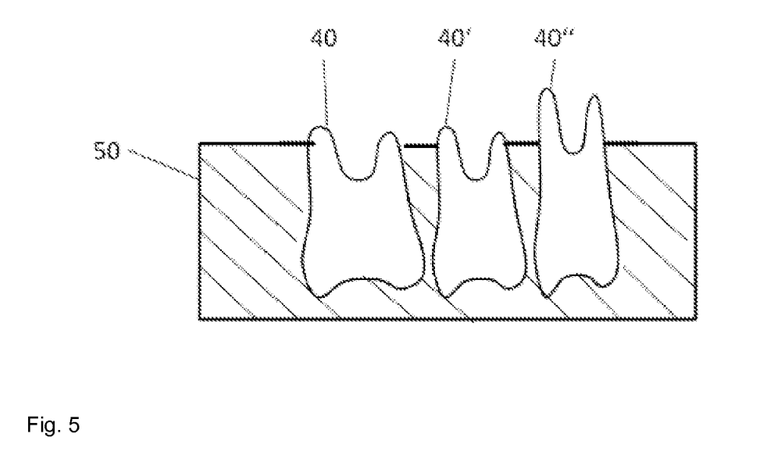
FIGS. 5 and 6 show a process of shortening the length dimension of the pre-fabricated tooth blanks by machining.

Based on the length difference data set 72 and further information concerning the external shape of the pre-fabricated tooth blanks 40, 40', 40" and the digital image 11 of the tooth situation, a digital image 51 of the negative mould 50 is created in the scope of step 400. This is illustrated in FIG. 4 as well. The digital image 51 enables a preparation 500, by machining, of the negative mould 50. The preparation 500, by machining, preferably is done by means of up-building and computer-based production method such as rapid prototyping. The pre-fabricated tooth blanks 40 are inserted into the negative mould 50 thus prepared in the scope of step 600, as is shown in FIG. 5.

Figure 6:
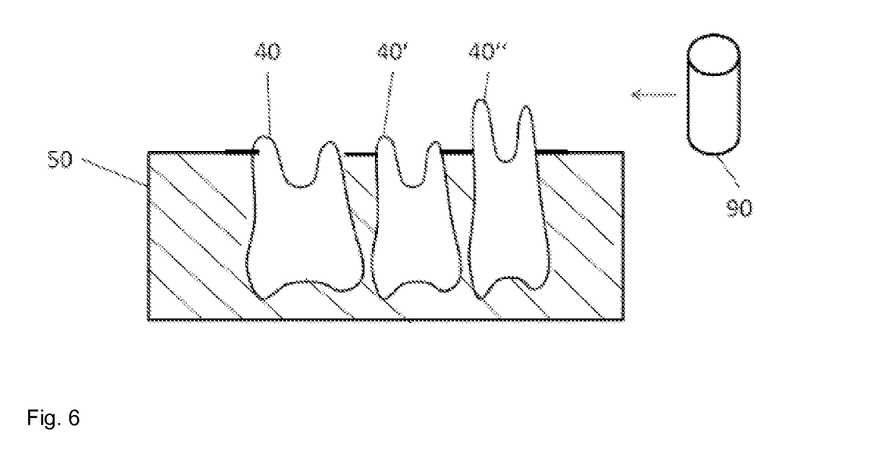

The negative mould 50 according to the invention holds the pre-fabricated tooth blanks 40, 40', 40" appropriately such that these project beyond the negative mould 50 on its basal side. A process of shortening 90 the pre-fabricated tooth blanks by machining by means of a milling machine, etc., proceeds in step 700. The pre-fabricated tooth blanks 40, 40', 40" are shortened by the length difference data set 72 in this process. As is evident from FIG. 6 in particular, the pre-fabricated tooth blanks 40, 40', 40" project beyond the negative mould 50 by said length difference data set 72. Accordingly, it is easy to ablate the projecting lengths. Concurrently, the negative mould 50 protects the outsides of the fractions of the pre-fabricated tooth blanks 40, 40', 40" that are to be inserted into the denture later on. Moreover, the negative mould 50 provides for mechanical stability and holds the pre-fabricated tooth blanks 40, 40', 40" during the shortening process in the scope of step 700. By this means, a precision of +/−20 µm, in particular +/−10 µm, can be attained in the shortening process. This high level of precision is a prerequisite for the creation of a denture 10 that can be used by the patient without any lengthy period of familiarisation.

Figure 7:
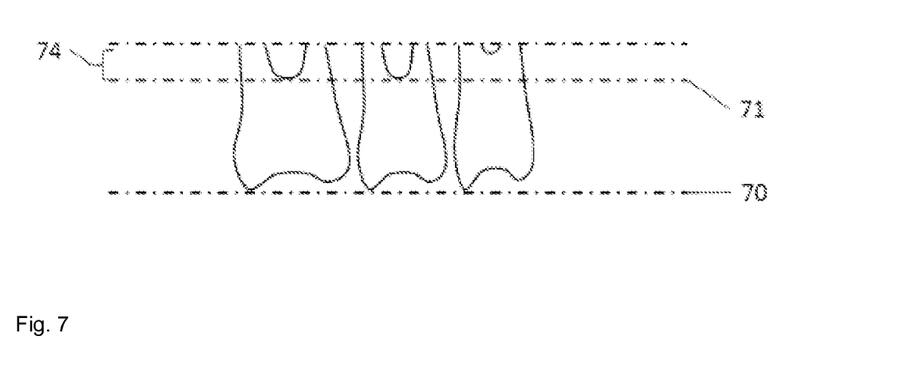
FIG. 7 shows the shortened tooth blanks.
Figure 8:
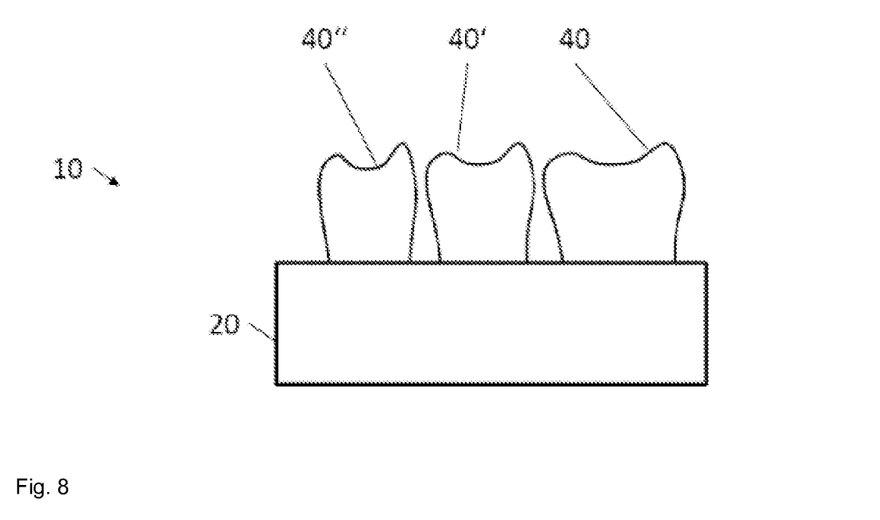
FIG. 8 shows a process of connecting the base element and the shortened tooth blanks to form the denture.

FIG. 7 shows the shortened tooth blanks. These are connected to a base element 20 in step 800 in order to create the denture 10 shown in FIG. 8. The denture 10 therefore consists of the base element 20, in which the shortened tooth blanks 40, 40', 40" are arranged.

REFERENCE NUMBERS

10 Denture
11 Digital model of the denture
15 Tooth or tooth situation or pre-defined tooth arrangement
20 Base element
40,40',40" Pre-fabricated tooth blanks
41,41'41" Digital representation of pre-fabricated tooth blanks
50 Negative mould
51 Digital image of the negative mould
52 Receptacles for tooth blanks in negative mould
70 Base line
71 Capital line
72 Length difference data set
74 Insertion depth
75 Tooth length
76 Actual tooth length of the tooth blank 40"
90 Shortening by machining
100 Preparation of a digital image
200 Shaping a digital model
300 Calculation of a length difference data set 400 Build-up of a digital image of a negative mould
500 Preparation of the negative mould by machining
600 Insertion of the pre-fabricated tooth blanks into the negative mould
700 Shortening of the pre-fabricated tooth blanks by machining
800 Connecting a base element and the shortened tooth blanks

The invention claimed is:

1. A method for producing a denture, wherein the denture comprises a base element that supports at least two tooth blanks, the method comprising:
   a. preparing the digital image of the tooth situation;
   b. computer-based generating of a digital model of the denture based on the digital image;
      by means of using and selecting digital representations of pre-fabricated tooth blanks;
      wherein the pre-fabricated tooth blanks have a defined length dimension;
   c. calculating a length difference data set, prepared from the defined length dimension and an insertion depth of the at least two pre-fabricated tooth blanks in the base element,
   d. building-up a digital image of a negative mould, in which the at least two prefabricated tooth blanks form the positive, wherein the negative mould encodes a position of the at least two pre-fabricated tooth blanks on the base element;
   e. producing, by machining, the negative mould by means of the digital image of the negative mould;
   f. inserting the pre-fabricated tooth blanks into the negative mould;
   g. shortening, by machining, the length dimension of the pre-fabricated tooth blanks from the basal side based on the length difference data set in order to produce the shortened tooth blanks; and
   h. connecting the base element and the shortened tooth blanks to form the denture.

2. The method according to claim 1, wherein, for preparing the negative mould, a computer-based up-building production method is utilized.

3. The method according to claim 2, wherein the computer-based up-building production method is selected from the group consisting of rapid prototyping, SD lithography, selective laser melting, 3D stereolithography, 3D inkjet, fused deposition modelling, 3D laser lithography and a combination of at least two thereof.

4. The method according to claim 1, wherein the pre-fabricated tooth blanks are held in the negative mould in at least one of a nonpositive fit manner, a form closure manner and a material bonded manner.

5. The method according to claim 1, wherein the method further comprises:
   preparing an attachment means for connecting the shortened tooth blanks to the base element, wherein the attachment means comprises a first coding means facilitating definite spatial positioning of the shortened tooth blank in the base part.

6. The method according to claim 5, wherein the negative moulds are provided with at least one second coding means facilitating definite spatial positioning of the pre-fabricated tooth blank in the negative mould.

7. The method according to claim 1, wherein, in step c, the selected digital representations of the tooth blanks are arranged on a crown side along a tooth line based on at least one of the tooth situation and a pre-defined tooth arrangement.

8. The method according to claim 1, wherein the method further comprises, after step b:
   adapting a height position of the digital representations of the pre-fabricated tooth blanks in the digital model of the denture.

9. The method according to claim 1, wherein the method further comprises:
   computer-based splitting of the digital model of the denture into a digital image of the base element and a digital image of the at least two tooth blanks.

10. The method according to claim 9, wherein the method further comprises:
    fabricating, by machining, the base element based on the digital image of the base element.

11. The method according to claim 1, wherein at least one of an ablating computer-based production method and an up-building computer-based production method is utilized in the method, wherein the at least one of the ablating computer-based production method and the up-building computer-based production method is selected from the group consisting of preparing the negative mould by machining and fabricating the base element by machining.

12. The method according to claim 1, wherein a digital image of a tooth situation that reflects a shape of a gingival area of a patient is utilized for shaping the digital model of the denture.

13. A non-transitory computer-readable data storage medium comprising instructions that enables a computer to execute the method according to claim 1.

14. A computer comprising the non-transitory computer-readable data storage medium according to claim 13.

* * * * *